(12) United States Patent
Liland et al.

(10) Patent No.: US 6,968,844 B2
(45) Date of Patent: Nov. 29, 2005

(54) MASK COVER

(75) Inventors: Frode Liland, Stavanger (NO); Bernt Kvam Randeberg, Stavanger (NO)

(73) Assignee: Laerdal Medical AS, Stavanger (NO)

( * ) Notice: Subject to any disclaimer, the term of this patent is extended or adjusted under 35 U.S.C. 154(b) by 181 days.

(21) Appl. No.: 10/365,218

(22) Filed: Feb. 12, 2003

(65) Prior Publication Data

US 2003/0226564 A1    Dec. 11, 2003

(30) Foreign Application Priority Data

Jun. 10, 2002    (NO) .................................. 2002 2760

(51) Int. Cl.$^7$ ............................................. A62B 7/10
(52) U.S. Cl. ......................... 128/206.16; 128/206.12; 128/206.17
(58) Field of Search ......................... 128/863, 205.25, 128/206.12, 206.16, 206.17, 206.21

(56) References Cited

U.S. PATENT DOCUMENTS

| | | | | |
|---|---|---|---|---|
| 364,394 | A | * | 6/1887 | Bright .................... 128/206.16 |
| 1,502,450 | A | * | 7/1924 | Wood .................... 128/206.13 |
| 1,837,591 | A | * | 12/1931 | Shindel ................. 128/206.16 |
| 2,149,067 | A | * | 2/1939 | Otero ........................... 128/863 |
| 4,579,113 | A | * | 4/1986 | McCreadie et al. .... 128/202.13 |
| 4,657,010 | A | * | 4/1987 | Wright .................. 128/205.25 |
| 4,827,924 | A | * | 5/1989 | Japuntich ............... 128/206.12 |
| 4,850,346 | A | * | 7/1989 | Michel et al. ......... 128/206.15 |
| 4,886,058 | A | * | 12/1989 | Brostrom et al. ...... 128/206.12 |
| 5,003,633 | A | * | 4/1991 | Itoh .................................. 2/9 |
| 5,062,421 | A | * | 11/1991 | Burns et al. ........... 128/205.27 |
| 5,517,986 | A | | 5/1996 | Starr et al. |
| 5,575,278 | A | * | 11/1996 | Bonhomme et al. ... 128/201.29 |
| 5,592,937 | A | * | 1/1997 | Freund .................. 128/206.16 |
| 5,794,617 | A | * | 8/1998 | Brunell et al. ......... 128/206.16 |
| 5,909,732 | A | * | 6/1999 | Diesel et al. .......... 128/206.24 |

FOREIGN PATENT DOCUMENTS

EP          1057494 A2     12/2000
WO       WO 00/35525       6/2000

* cited by examiner

Primary Examiner—Aaron J. Lewis
(74) Attorney, Agent, or Firm—Frommer Lawrence & Haug LLP

(57) ABSTRACT

A cover, for a flexible patient breathing mask, which is made predominantly of a soft material and has an open bottom and an internal shape corresponding to the external shape of a patient mask. The cover has a socket piece opening opposite the open bottom. The socket piece opening corresponds to the socket piece on a patient mask. Openings are formed in the side faces of the cover, which allow visual access to the patient mask. The chin and cheek sections of the cover are deformable so that the mask is capable of distorting the cheek and chin sections of the breathing mask so that the mask is tightly fitted against the anatomy of the face of the patient to alter the shape of the cover through the application of force. The side edges of the cover may include at least one fastening device for straps for holding the cover and the mask tight against a patient's face, where the fastening device(s) may be hook-shaped.

19 Claims, 1 Drawing Sheet

MASK COVER

FIELD OF THE INVENTION

The present invention relates to a retaining cover for a flexible patient mask, and more particularly, to a retaining cover for a flexible patient mask which assists the attending personnel in achieving an improved seal between the patient's face and the mask for all of the various differences in facial anatomies.

BACKGROUND OF THE INVENTION

The use of breathing masks to secure a supply of oxygen is well known in connection with resuscitation, operations, and other medical and rescue procedures. These masks typically include soft parts often made from silicon, PVC or similar material, and which are therefore flexible enough to be adapted to a patient's anatomy in order to obtain a tight-fitting mask against the anatomy of the patient's face. The masks are usually retained in their proper position by straps that extend behind the head of the patient. These straps are either attached to the corners of the actual mask by means of suitable fixtures, or to a separate strap having a retaining ring arranged around the socket piece of the mask. Typically, the socket piece is a pipe stub adapted for connection to a breathing device protruding from the face of the mask. In designs where the mask has been entirely formed of soft materials, it has been found to be difficult to fasten the fixtures to the actual mask.

OBJECTS OF THE INVENTION

It is therefore an object of the present invention to provide a cover for retaining a patient breathing mask which avoids the aforementioned deficiencies of the prior art.

It is also an object of the present invention to provide a cover for retaining a patient mask which obtains a tight-fit of the mask against the anatomy of the patient's face.

It is a further object of the present invention to provide a cover for retaining a patient mask that assists the attending personnel in achieving an improved seal between the patient's face and the mask, especially in the case of patients with difficult anatomies, such as patients with a pointed chin or hollow cheeks.

Various other objects, advantages and features of the present invention will become readily apparent from the ensuing detailed description and the novel features will be particularly pointed out in the appended claims.

SUMMARY OF THE INVENTION

A cover for retaining a flexible patient breathing mask includes deformable cheek and chin sections which are capable of distorting the cheek and chin sections of the breathing mask so that the mask is tightly fitted against the anatomy of the face of the patient. The cover also includes a socket piece opening through which a socket piece on the patient breathing mask can be received such that the cover is retained in place on the breathing mask and clear access to the mouth of the patient is provided.

The cover is used to brace the outer walls of the mask, and may be transparent and/or have openings that provide an unobstructed view through the cover and the silicon mask, of the patient's lips, etc. The cover increases the rigidity of the mask in the direction of pressure, and distributes forces evenly around the circumference of the mask, thereby enhancing the convenience of use for the attending personnel when using the mask on a patient whose facial anatomy is difficult.

By making it possible to alter the shape of the cover by applying force, the attending personnel may press the sides of the cover together in order to make the underlying mask narrower to provide an improved seal between the patient's face and the mask.

By applying force of the more rigid cover the flexible mask, it is possible to alter the shape of the cover allowing the attending personnel to alter the shape of the mask as necessary to insure a substantially air tight fit of the mask.

The sides of the cover may incorporate hooks for attaching straps that retain and force the mask with the cover tight against the patient's face. However, the mask can also be provided with other means of attaching straps, such as, a strap retaining ring.

BRIEF DESCRIPTION OF THE DRAWINGS

The following detailed description, given by way of example, but not intended to limit the invention solely to the specific embodiments described, may best be understood in conjunction with the accompanying drawings in which.

DETAILED DESCRIPTION OF CERTAIN PREFERRED EMBODIMENTS OF THE INVENTION

Figure 1:
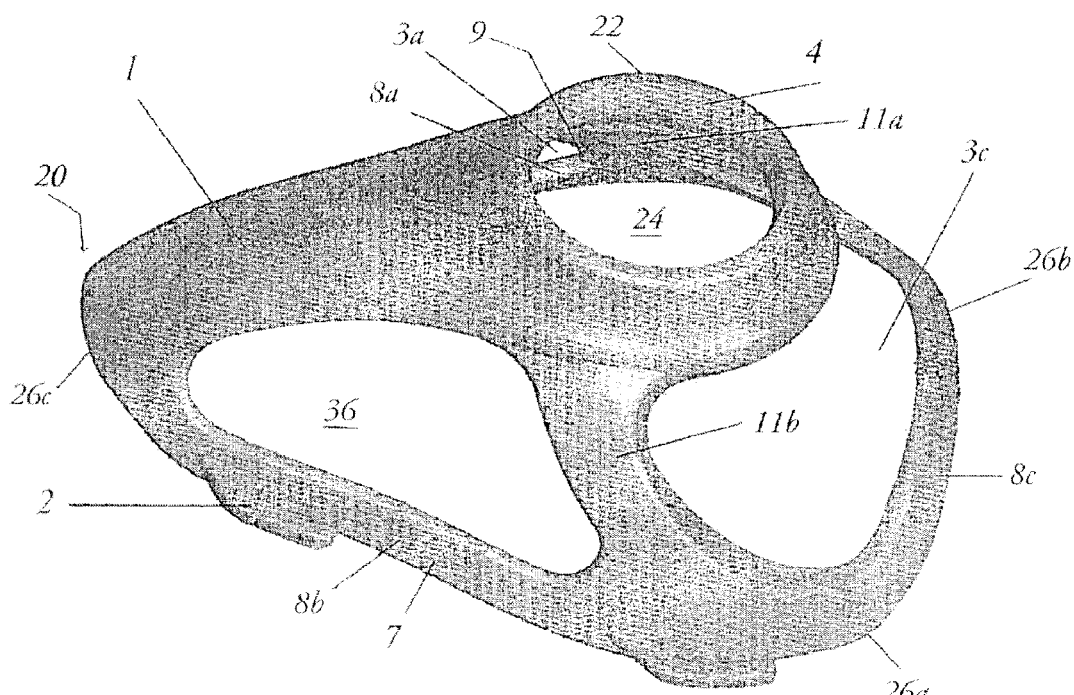
FIG. 1 is a front perspective view of a preferred embodiment of a retaining cover for a flexible patient mask in accordance with the teaching of the present invention.
Figure 2:
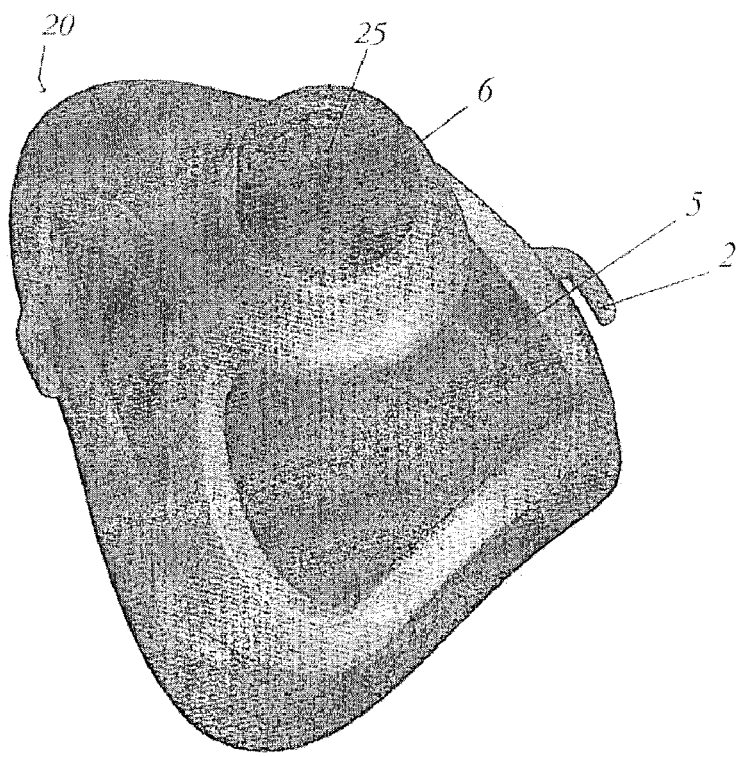
FIG. 2 is a front perspective view of the retaining cover of FIG. 1 according to the invention placed on a flexible patient breathing mask.

Referring now to FIGS. 1 and 2 of the drawings, wherein like reference numerals represent like features in the several views, a cover 20 for retaining a patient breathing mask 5 in accordance with the teachings of the present invention is shown. FIG. 1 specifically shows the cover 20 in a position removed from the patient breathing mask. FIG. 2 illustrates the cover 20 retaining a patient breathing mask 5 so as to obtain a tight fit of the mask 5 against the anatomy of the patient's face.

More specifically, FIG. 1 shows a cover 20 according to the invention having an opening 4 in the top side 22 thereof, the dimensions of which correspond to those of the socket piece 6 of the patient breathing mask 5 such that the socket piece 6 of the patient breathing mask 5 can extend therethrough, preferably with a tight fit. As a result, when the cover 20 is placed on the breathing mask 5, the cover 20 is securely held in place on the breathing mask 5.

In the embodiment shown, the cover is designed with a trilateral pyramidal form having an open bottom 24 and rounded edges 26a, 26b, and 26c, which conform generally to the external shape of a breathing mask 5. A nose section 1 of the cover 20 extends down from the opening 4 towards the open bottom 24. Cheek openings 3a and b are formed on either side of the cover 5, in respective side faces 7 and 9. A main chin opening 3c is formed opposite of the nose section 1 in a chin section 10. The lower edges of the opening 3a, 3b, and 3 define strip-shaped cheek sections 8a and 8b are formed on either side of the cover 5 and a strip-shaped chin section 8c which in use abut against the cheek sections and chin section, respectively, of the breathing mask (see FIG. 2). Between each cheek opening 3a and b and the chin opening 3c, a web member is provided, such as web members 11a and 11b, that respectively connect the cheek sections 8a and 8b and the chin section 8c to the top side 22 of the cover.

The openings 3a, 3b and 3c allows visual access to the mask 5, and the opening 25 in the socket piece 6 in the mask 5 allows visual access to the patient's lips etc. The cheek sections 8a and b and the chin section 8c may be deformed relative to the top part 22 of the otherwise inflexible cover. As openings are formed in the cover 20 to allow visual access to the patient mask 5, the cover 20 does not have to be made from transparent plastic. Therefore, the present cover 20 provides for more flexibility in the choice of the cover material. Thus, the cover material can be made of various suitable materials. However, the selected material must allow the cover to exhibit a certain amount of stiffness while also allowing itself to be deformed upon the application of a certain amount of force.

When the attending personnel uses the mask 5 with the cover 20 according to the preferred embodiment of the present invention on a patient whose facial anatomy is particularly difficult, e.g., with a pointed chin or hollow cheeks, the cover 20 and mask 5 are pressed together by pressing the deformable web members 11a and 11b of the cover 20 towards each other with the fingers of the attending personnel. This distorts the chin section 10 in a manner such that the curve sharpens and adapts to the shape of the chin. The deformable cheek sections 8a and 8b are pressed towards each other, and thereby against the hollow cheeks.

As shown in FIGS. 1 and 2, the lower portions of the side faces 7 and 9 include hooks 2 for attaching straps.

Naturally, it is possible, instead of using a deformable cover, that the covers could be shaped in accordance with the difficulty anatomy of a patient. Such as solution would allow a standard silicon mask with an adapted cover to be used on any patient, including patients with difficult anatomies, without encountering problems.

Preferably, the covers are designed to be stacked and thereby occupy a minimal amount of space, for instance, in an ambulance.

Therefore, in accordance with one of the general objects of the present invention, a retaining cover for a flexible patient breathing mask has been provided which obtains a tight-fit of the mask against the anatomy of the patient's face. In addition, this retaining cover assists the attending personnel in achieving an improved seal between the patient's face and the mask, especially in the case of patients with difficult anatomies, such as patients with a pointed chin or hollow cheeks.

Although the invention has been particularly shown and described with reference to certain preferred embodiments, it will be readily appreciated by those of ordinary skill in the art that various changes and modifications may be made therein without departing from the spirit and scope of the invention. It is intended that the appended claims be interpreted as including the foregoing as well as various other such changes and modifications.

What is claimed is:

1. A cover for retaining a flexible patient breathing mask and which is formed substantially of a soft material, the mask having a socket piece capable of communicating gas into the mask, the cover and the mask being separate parts, said cover comprising:
   an open bottom;
   deformable cheek sections and a deformable chin section providing a shape to the cover which is capable of corresponding to the external shape of the patient breathing mask; and
   a socket piece opening opposite the open bottom through which the socket piece on the patient breathing mask can be received such that the cover is retained in place on the breathing mask and clear access to the mouth of the patient is provided.

2. The cover according to claim 1, wherein said cover has side faces extending between said socket piece opening and said open bottom, said side faces including cheek openings.

3. The cover according to claim 1, wherein said side faces include deformable side web members of said deformable cheek section which distort the cheek section of the mask to conform to the anatomy of the cheeks of the patient.

4. The cover according to claim 1, wherein generally longitudinally-aligned web members of said deformable chin section can distort a deformable chin web member of said deformable chin section which thereby conforms the chin section of the mask to the anatomy of the chin of the patient.

5. The cover according to claim 1, wherein each of said cheek and chin sections have an opening to provide visual access to the patient mask.

6. The cover according to claim 1, and further comprising at least one fastening device for retaining straps which hold the cover and the mask tight against a face of the patient.

7. The cover according to claim 6, wherein the at least one fastening device is hook-shaped.

8. The cover according to claim 7, wherein a plurality of the hook-shaped fastening devices extend from the at least one deformable cheek section.

9. The cover according to claim 6, wherein the fastening device is ring-shaped.

10. A cover for retaining a flexible patient breathing mask, the mask having a socket piece capable of communicating gas into the mask, the cover and the mask being separate parts, comprising deformable cheek and chin sections which are capable of distorting the cheek and chin sections of the breathing mask so that the mask is tightly fitted against the anatomy of the face of the patient, and further comprising a socket piece opening through which the socket piece on the patient breathing mask can be received such that the cover is retained in place on the breathing mask and clear access to the mouth of the patient is provided.

11. The cover for retaining a flexible patient breathing mask of claim 10, wherein said deformable cheek sections include a pair of side web members which can be pressed together so as to conform the cheek sections of the patient mask to the cheek of the patient.

12. The cover for retaining a flexible patient breathing mask of claim 11 wherein said deformable chin section includes a pair of generally longitudinal web members extending between said pair of side web members and said socket piece which can be pressed toward each other so as to deform a chin web member extending between said side web members to thereby conform the chin section of the patient mask to the chin of the patient.

13. The cover for retaining a flexible patient breathing mask of claim 10 wherein each of the said cheek and chin sections have an opening to provide visual access to the patient mask.

14. The cover for retaining a flexible patient breathing mask of claim 10 wherein the cover is of a trilateral pyramidal form having an open bottom and rounded edges which conform generally to the external shape of the breathing mask.

15. A cover for retaining a flexible patient breathing mask, the mask having a socket piece capable of communicating gas into the mask, the cover and the mask being separate parts, comprising:
- deformable cheek sections including a pair of side web members which can be pressed together so as to conform the cheek sections of the patient mask to the cheeks of the patient;
- a deformable chin section including a pair of generally longitudinal web members which can be pressed toward each other so as to deform a chin web member extending between said side web members to thereby conform the chin section of the mask to the chin of the patient; and
- wherein said deformable cheek and chin sections are capable of distorting the cheek and chin sections of the breathing mask so that the mask is tightly fitted against the anatomy of the face of the patient.

16. The cover for retaining a flexible patient breathing mask of claim 15 wherein each of said cheek and chin sections have an opening to provide visual access to the patient mask.

17. The cover for retaining a flexible patient breathing mask of claim 15 and further comprising a socket piece opening through which a socket piece on the patient breathing mask can be received such that the cover is retained in place on the breathing mask and clear access to the mouth of the patient is provided.

18. The cover for retaining a flexible patient breathing mask of claim 15, and further comprising at least one fastening member for retaining straps which hold the cover and mask tight against a face of a patient.

19. The cover for retaining a flexible patient breathing mask of claim 18, wherein at least one fastening device is hook-shaped.

* * * * *